US00PP17396P3

(12) United States Plant Patent
Sonnenberg

(10) Patent No.: US PP17,396 P3
(45) Date of Patent: Feb. 6, 2007

(54) MUSHROOM VARIETY NAMED 'BRONCOH'

(50) Latin Name: *Agaricus bisporus Imbach*
Varietal Denomination: Broncoh

(75) Inventor: Anton Sonnenberg, Leunen (NL)

(73) Assignee: Praktijkonderzoek Plant & Omgeving B.V., Wageningen (NL)

( * ) Notice: Subject to any disclaimer, the term of this patent is extended or adjusted under 35 U.S.C. 154(b) by 67 days.

(21) Appl. No.: 10/848,745

(22) Filed: May 19, 2004

(65) Prior Publication Data

US 2005/0262612 P1 Nov. 24, 2005

(51) Int. Cl.
*A01H 15/00* (2006.01)

(52) U.S. Cl. ..... Plt./394

(58) Field of Classification Search ..... Plt./394
See application file for complete search history.

(56) References Cited

PUBLICATIONS

Hit on 'Broncoh', UPOV–Rom, GRI Jouve Retrieval Software, Plant Variety Database, 2004/02.*

* cited by examiner

*Primary Examiner*—Anne Marie Grunberg
(74) *Attorney, Agent, or Firm*—The Webb Law Firm, P.C.

(57) ABSTRACT

A new and distinct *Agaricus bisporus Imbach* mushroom cultivar known by the variety name 'Broncoh' that has a yield that is on average 25–28% higher than the present-day commercial brown strains and produces fruiting bodies which are firm and have a good shelf life.

8 Drawing Sheets

Botanical classification: *Agaricus bisporus Imbach.*
Varietal denomination: 'Broncoh'.

BACKGROUND OF THE INVENTION

The present invention comprises a new and distinct cultivar of mushroom of the Species *Agaricus bisporus* (Lange) *Imbach* (button mushroom) named 'Broncoh'. The new variety is of the Fungi Kingdom, the Basidomycotina Phylum, and the Agaricaceae Family.

The button mushroom of commerce (*Agaricus bisporus*) is one of the most commercially cultivated mushrooms worldwide (estimated world production of 2 million metric tons in 2002). It is grown on a substrate called compost. This substrate consists of wheat straw, horse manure, chicken manure, gypsum and water and is fermented in tunnels in three phases. The substrate is inoculated with spawn. Spawn consists of grain (usually wheat) that is boiled in water, sterilized and inoculated with a pure culture of vegetative mycelium. After the grain is fully colonized the spawn is stored at 4 to 8° C. in plastic bags of 15 kg before being used to inoculate substrate. The spawn production is done in especially equipped plants on a large scale. Spawn is mixed with phase II compost and colonized in tunnels at 26° C. The full grown compost (spawn run compost) is transported to growing houses and filled in beds (usually two rows of shelfs, 4 to 6 high, and 90 to 100 kg of compost/m$^2$). The growing houses are equipped with climate control systems. The fully colonized compost is covered with a casing soil layer of approximately 5 cm thickness. The casing soil consists of peat and lime. After the colonization of the casing soil (10 days at 26° C., with hardly no air movement) the climate in the growing house is changed to initiate fruiting body formation. The air temperature is decreased to 16–18° C. by venting the air (letting in of fresh air from outside the growing house). After 10to 14 days mushrooms are picked either by hand (for the fresh market) or cut and harvested mechanically (for canning). Two types of strains are cultivated world wide, i.e. white and brown strains producing mushrooms with a white or brown cap color, respectively. Within the white strains, three types of varieties are cultivated, whereas within the brown strains, only one variety is used. The brown strains are either picked at an early developmental stage or when fully matured. In the former case, mushroom caps are usually closed. In the latter case, caps are fully open so that the gills, producing the spores, are fully exposed. These types of mushrooms are designated as Portabellos or Portabellas.

The life cycle of *A. bisporus* has been well studied in the past. The compatibility of strains is controlled by one mating-type factor and different alleles are needed for fertility. Fertile vegetative mycelium consists of a network of cells, each of which has a variable number of two genetically distinct nuclei with opposite mating type (heterokaryon). In the basidia, specialized cells on the lamellae that produce spores, the number of nuclei is reduced to two, one of each mating type. After nuclear fusion, a normal meiosis takes place. Most basidia, however, produce two spores, each containing two non-sister nuclei (n+n). Fruiting tests show that these single spore cultures can produce mushrooms, i.e. that they contain both mating types. Besides this heteroallelism for the mating type, *A. bisporus* maintain in general the parental heterogeneity. This can be explained by assuming that there is a mechanism that favors the pairing of non-sister nuclei and that there is a low percentage of recombination in meiosis. The former is supported by microscopic observations that show a meiotic spindle orientation resulting in 80% of the spores incorporating non-sister nuclei. Several reports have also shown an unusually low recombination in *A. bisporus*. Only a small percentage of the basidia produce 3 or 4 spores. Most of these spores are haploid (n) and do not fruit or form only a limited number of fruit bodies. Single spore cultures derived from these types of spores produce a vegetative mycelium that also contain a variable number of (genetically identical) nuclei per cell (homokaryon). This secondary homothallic life cycle is found in all commercial lines and in field isolates from Alberta, coastal California and France. Other characteristics of *A. bisporus* are, besides the variable number of nuclei in both homo- and heterokaryons, the lack of clamp connections in heterokaryons. The typical life cycle and the lack of differences between homo- and heterokaryons are a serious drawback in breeding.

The purpose of this breeding program was to construct a brown strain that has a yield comparable to the white strains. That is because strains that are used for the production of brown mushrooms have a yield that is, on average, 20–25% lower than strains that produce white mushrooms. The new variety has been trial and field tested and has been found to retain its distinctive characteristics and remain true to type through successive propagations.

DESCRIPTION OF THE DRAWINGS

The accompanying photographic drawings illustrate the new cultivar, with the color being as nearly true as is possible with color illustrations of this type:

FIG. 4 illustrates the differences between the colors of caps and stipes of 'Broncoh' and comparison varieties;

FIG. 6 illustrates the differences in the color of spores of the new variety and comparison varieties;

FIG. 8 illustrates the discoloration of flesh and lamellae after cutting 'Broncoh'.

DETAILED DESCRIPTION OF THE INVENTION

Figure 1:
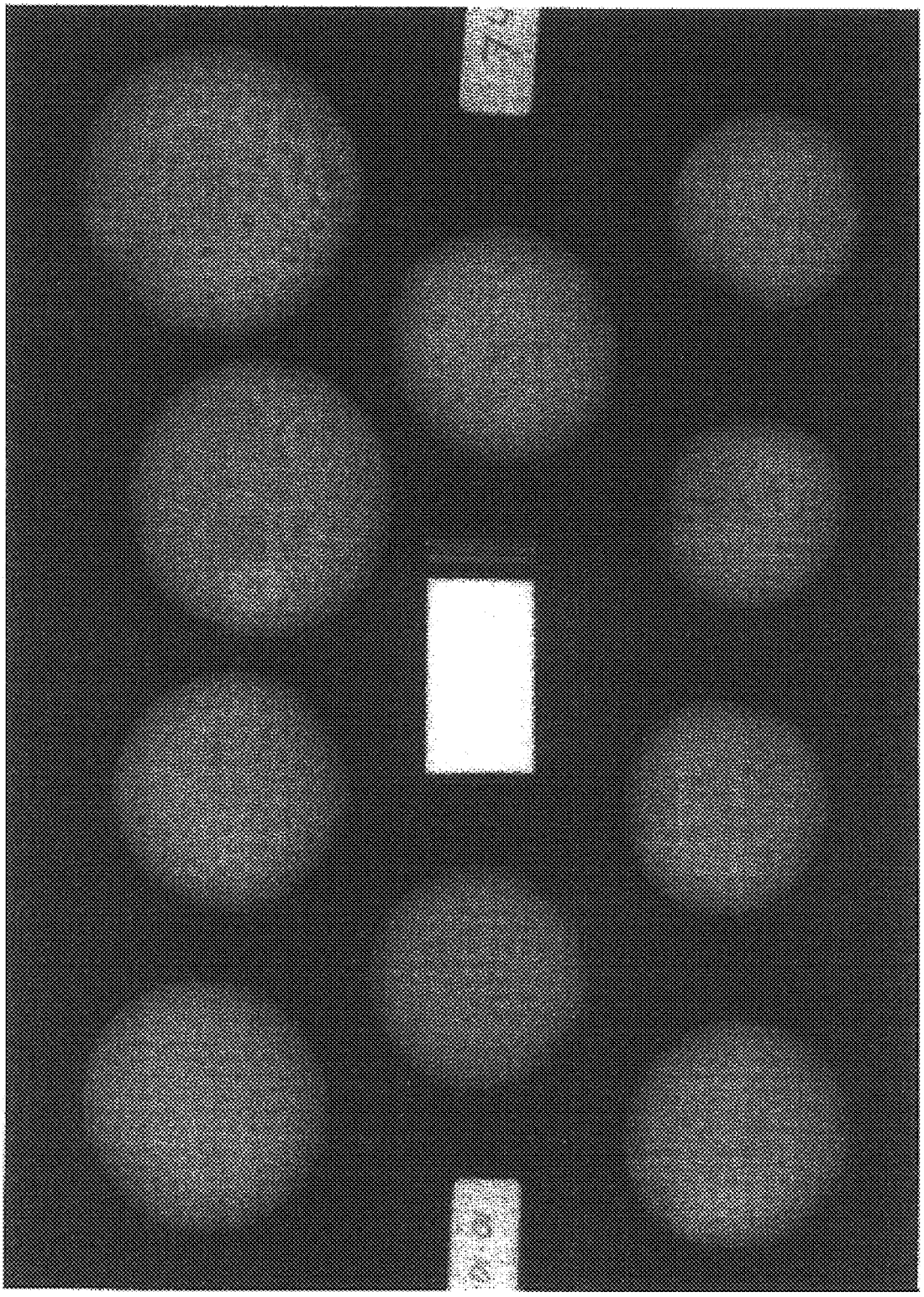
FIG. 1 illustrates a top view of the 'Broncoh' mushrooms, wherein the color and scaling can be clearly seen.
Figure 2:
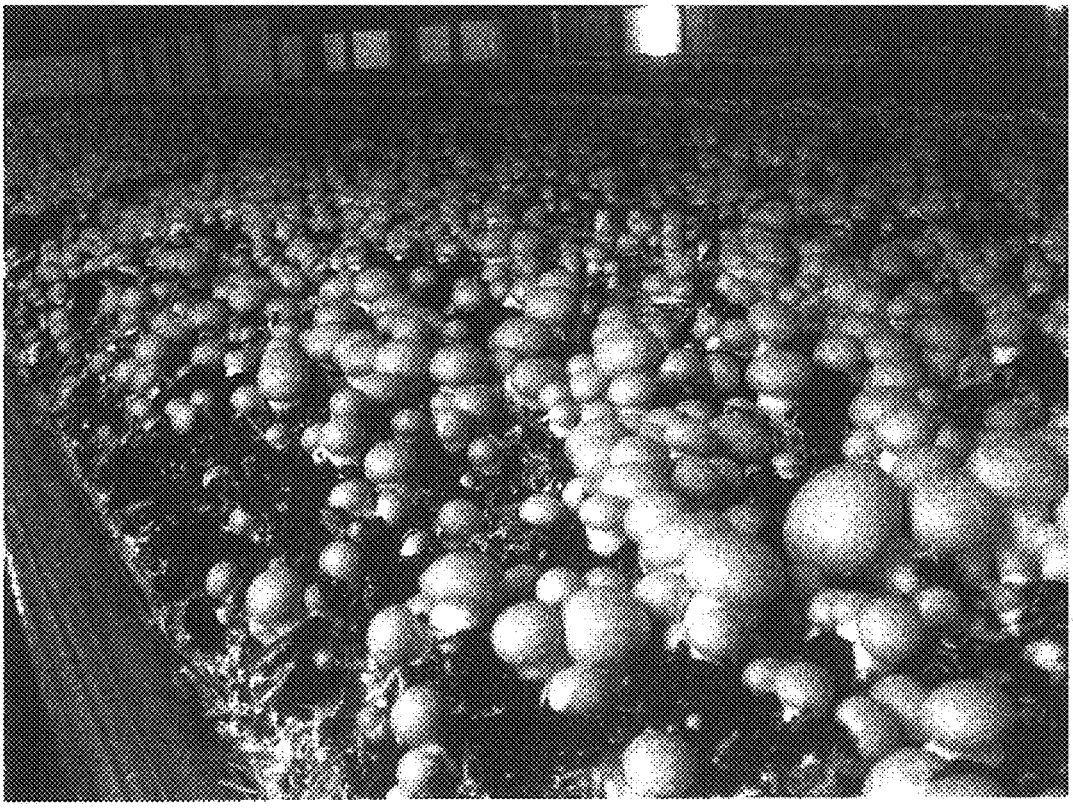
FIG. 2 illustrates a first flush of 'Broncoh' in a typical Dutch shelf system.

The following detailed description sets forth the breeding procedures and the characteristics of the new cultivar. The strain is maintained and propagated as vegetative mycelium. Spawn (inoculum for the substrate compost) is prepared from the vegetative mycelium. The new variety was tested on a commercial scale in May–June 2003.

The breeding program was carried out in Horst-America, The Netherlands in 1999–2000. Three homokaryotic strains were used for breeding. Two parental strains of the commercial white button mushroom, strain Horst U1 (homokaryon H39 and homokaryon H97, also known as Somycel 53 and Somyal 9.2). The third homokaryon was isolated from a wild brown strain, strain MES-101. This homokaryon was isolated by protoplasting vegetative mycelium of the brown strain and recovering protoclones (colonies, each derived from a single regenerated protoplast). The used homokaryons are not derived from patented strains.

The homokaryons H39 and H37 were crossed with the homokaryon derived from the wild isolate. Both crosses were cultivated on a small scale and spores were collected. Spores were diluted in water and plated on malt extract agar. After germination, single spore isolates (SSIs) were selected, preferentially those that grow slowly. The slowly growing SSIs usually contain one nuclear type, are thus homokaryotic and suitable for mating, thus breeding. Previously, we have generated a molecular marker that is linked to the cap colour. From both sets of homokaryotic SSIs, selections were made for brown cap colour and mating type of the wild homokaryon. The selected SSIs were backcrossed to their respective commercial homokaryon, i.e. H39 or H97. These hybrids were cultivated on a small scale and the best of each set was used to produce spores. From both spore prints, the SSIs were isolated that had the marker for brown cap colour and the mating type for the commercial homokaryons. In the last breeding step, the homokaryons of one set were crossed with the homokaryons of the other set in all possible combinations. The hybrids were tested in four replicas on trays of 1.3 $m^2$. The best strain was designated 'Broncoh' and is the subject of this plant patent application. The variety 'Broncoh' has been submitted for Plant Breeders' Rights at the Community Plant Variety Office of the European Community on Aug. 28, 2001. The Office has accepted the submission but no tests have been performed yet by the Office.

The first asexual reproductions of 'Broncoh' occurred in May through June of 2003 in America, The Netherlands. The strain was tested in 2003 at three farms on a commercial scale. For this, the spawn was made by a commercial spawn producer and the spawned compost by a commercial compost producer.

The mature cap shape of 'Broncoh' is oblate spheroid to flat. The immature cap shape of 'Broncoh' is round to oblate spheroid. The cap diameter ranges from 30–40 mm, with an average of 35 mm. The mature color of 'Broncoh' is 73.0, 10.3, 18.4 (L, a, b). Scales are located on the surface of the cap and are the same color as the mature cap.

Table 1 illustrates distinguishing characteristics between the claimed variety and its antecedents:

| | Somycel 53 | Somycel 9.2 | MES-101 | Broncoh |
|---|---|---|---|---|
| Scaling of cap | smooth | scaling | Scaling between So, 53 and Som 9.2 | Scaling between So, 53 and Som 9.2 |
| Color of cap | White | Off-white | Dark brown | Yellow-brown |
| Yield | 25 kg/$m^2$ | 30 kg/$m^2$ | 20 k/$gm^2$ | 22 kg/$m^2$ |
| Cap width | 26 mm | 34 mm | 28 mm | 38 mm |
| Stipe length | Short | long | Short | 17 mm |

*The old strains Somycel 53 and Somycel 9.2 were not recently tested. Data were obtained from experiments done approximately 30 years ago and are thus indicative.

Additionally, the following distinctive characteristics of the new variety were observed by the commercial growers:

1. The strain has a yield that is on average 25–28% higher than the present-day commercial brown strains (compared to commercial lines Sylvan C38, Le Lion C9 and Amycel 2400, all unpatented), as shown in Table 3;
2. The production of mushrooms is spread over 3 to 5 days which allows a hand picking of good quality. This spread of production is comparable to the commercial brown lines;

3. The strain produces fruiting bodies which are firm and have a good shelf life. These characteristics are better than those of the commercial lines;
4. The strain produces mushrooms that have a higher weight on average per fruiting body than those produced by commercial lines. The fruiting bodies were compared at identical developmental stages. This means that picking costs for 'Broncoh' are lower than for commercial lines; and
5. The caps of 'Broncoh' show more scaling than commercial lines, especially in the first flush.

Other characteristics of 'Broncoh' distinguishable from other varieties and types of differences observed include (compared to commercial lines Sylvan C38, Le Lion C9 and Amycel 2400, all unpatented):

1. The color of the caps of 'Broncoh' is lighter and of a yellow-brown color, whereas the commercial brown strains have a dark brown color. The cap color of 'Broncoh' varies in the flushes from 61 to 72 reflection. Brown commercial strains vary from 61 to 70;
2. 'Broncoh' has better shelf life than the comparison commercial brown strains: loss of weight after storing for one week at 4° C. was 50% less than that of the commercial brown strains; and
3. The firmness of picked 'Broncoh' mushrooms was also preserved better during storage of one week than fruit bodies of the comparison commercial brown strains. Also, the firmness of fruiting bodies of 'Boncoh' is higher than the comparison commercial brown strains at identical developmental stages.

BOTANICAL DATA COLLECTION CONDITIONS AND STANDARDS

The color standard used in the present application is the L*a*b* method (also designated as CIE.LAB or CIE-L*a*b*) defined by "Commission International de l'Eclaire" in 1976. The location where measurements were made was Horst-America, The Netherlands. Light conditions where measurements were made were by artificial light in a light cabinet with adjustable and standardized light conditions.

ADDITIONAL BOTANICAL DATA FOR MUSHROOM STRAIN "BRONOCH"

To obtain additional botanical data on mushroom strain "Broncoh", the mushroom was grown on commercially available compost according to current commercial practice. After 16 days of spawn run at 24° C. a commercially available casing soil (peat and lime stone) was applied. The casing soil was CAC-ed at 1.25 kg/m$^2$. After 4 days of colonization, the casing soil was ruffled and 3 days later the cultures were vented. Mushrooms were harvested as quality 1 (cap diameter 30–60 mm, velum intact but not stretched) and used for measurement of color and dimensions. A few mushrooms were allowed to develop further, allowing the production of spore prints. Strain Broncoh was compared to strains C9 (a brown commercial strain) and U1 (a commercial white strain).

Figure 3:
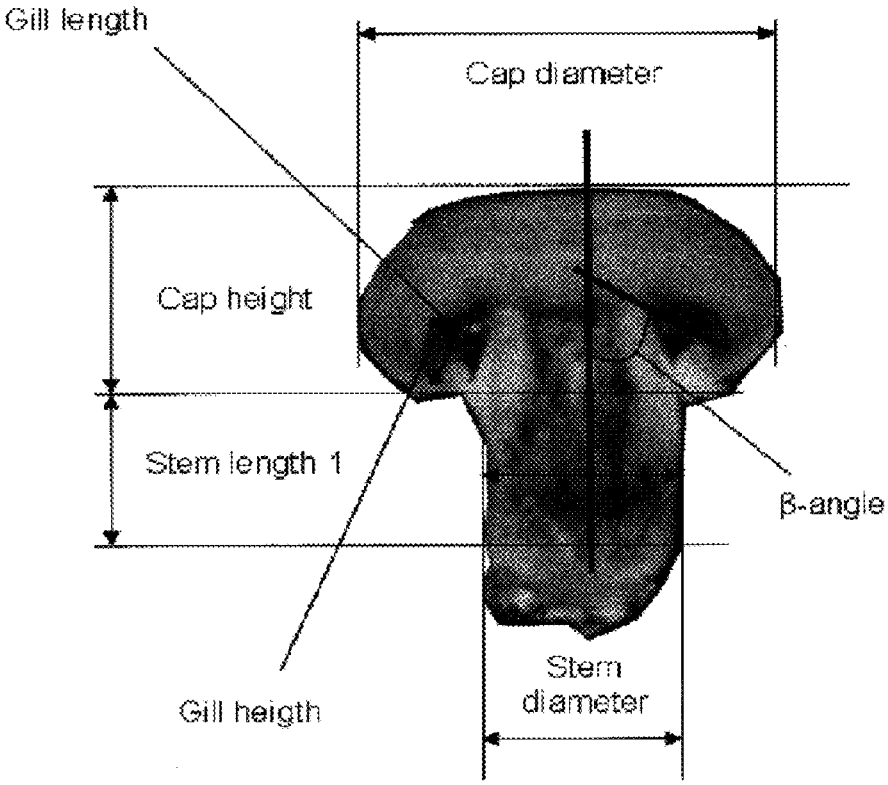
FIG. 3 illustrates a sliced transverse view of the new variety along with an overview of the different dimensions measured on 'Broncoh' and comparison varieties.

The dimensions were measured as shown in FIG. 3 using computer image analysis. The "beta" angle is used as a measure of developmental stage of the mushrooms (Umar & Van Griensven, 1996). As a second measure of developmental stage, we used the open area between the gills and the velum (expressed as % of the cap area (van Loon P. C. C., 1996). This measure of developmental stage was linked to the classification of developmental stages as described by Hammond & Nichols (1976).

Color measurements were done either on whole mushrooms using a Minolta Chromameter or on sliced mushrooms using computer image analysis (van Loon, 1996). Cap color was measured on top of whole mushrooms. Stipe color was measured on the outside of stipes that were cut longitudinally and placed on a hard surface with the outside of the stipe facing up. Spore color was measured using a Minolta Chromameter. Spores were collected from several mushrooms and scraped together to form a thick layer. On top of this layer a glass plate was placed to provide an even surface.

Results

Dimensions and Developmental Stage

The dimensions of the mushrooms of strains Broncoh, C9 and U1 are shown in Table 2. For all strains studied mushrooms were harvested at the same cap width. At this given cap width, there are differences between the strains with respect to developmental stage. Strains Broncoh and C9 have a more advanced developmental stage as compared to U1.

Differences in dimensions of the mushrooms are found in cap height and width of stipe and lamellae. Strain U1 has a slightly but statistically significant higher cap than strains Broncoh and C9. Strain C9 has a slightly but statistically significant broader stipe than strain Broncoh. There is also a large difference between the stipe width of strain C9 and strain U1. This difference is not statistically significant (just barely).

With respect to width of the lamellae, strain Broncoh has slightly but statistically significant higher lamellae than strains C9 and U1.

TABLE 2

Dimensions of the mushrooms of strains Broncoh, C9 and U1. ($^x$significant difference with strain Broncoh at p = 0.05).

| | Broncoh | | | C9 | | | U1 | | |
|---|---|---|---|---|---|---|---|---|---|
| STRAIN | Mean | N | Std. Deviation | Mean | N | Std. Deviation | Mean | N | Std. Deviation |
| CAP WIDTH (MM) | 38.1 | 20 | 2.5 | 38.1 | 20 | 2.5 | 39.3 | 20 | 3.3 |
| CAP HEIGHT (MM) | 24.3 | 20 | 1 | 24.2 | 20 | 1.3 | 25.3$^x$ | 20 | 1.2 |
| STIPE WIDTH (MM) | 16.5 | 20 | 1 | 17.6$^x$ | 20 | 1.3 | 17.3 | 20 | 1.7 |
| STIPE LENGTH (MM) | 17.7 | 20 | 3.7 | 15.9 | 20 | 2.7 | 17.1 | 20 | 4.2 |
| LAMELLAE LENGTH (MM) | 9.7 | 20 | 0.8 | 9.7 | 20 | 0.8 | 9.9 | 20 | 1.1 |
| LAMELLAE WIDTH (MM) | 3.2 | 20 | 0.3 | 2.9$^x$ | 20 | 0.3 | 2.9$^x$ | 20 | 0.4 |
| BETA ANGLE (°) | 36.5 | 20 | 3.3 | 47.9$^x$ | 20 | 4 | 42.3$^x$ | 20 | 2.5 |
| DEVELOPMENTAL STAGE | 3.34 | 20 | 0.8 | 3.76 | 20 | 1.1 | 2.7$^x$ | 20 | 0.8 |

Color of Cap and Stipe

Figure 5:
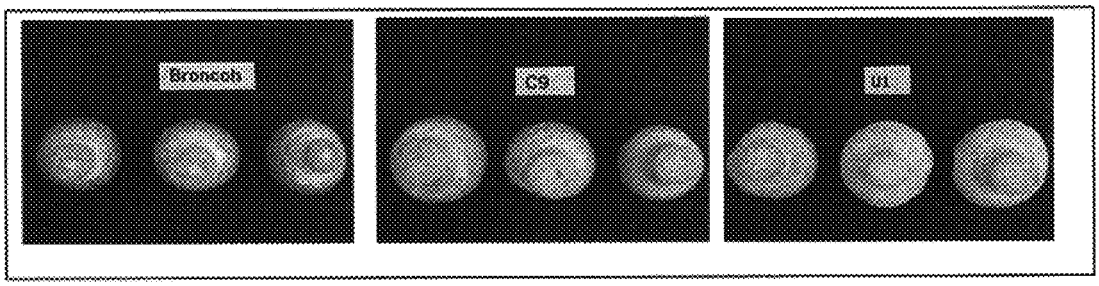
FIG. 5 illustrates the veils of mushrooms from 'Broncoh', C9 and U1.

Color of cap and stipe are shown in FIG. 4. Strains Broncoh and C9 both have a brown cap, whereas strain U1 has a white cap. Strain C9 produces slightly darker brown mushrooms than strain Broncoh. The veils of the mushrooms of all three strains are predominantly white as shown in FIG. 5.

Color of Spores

Figure 7:
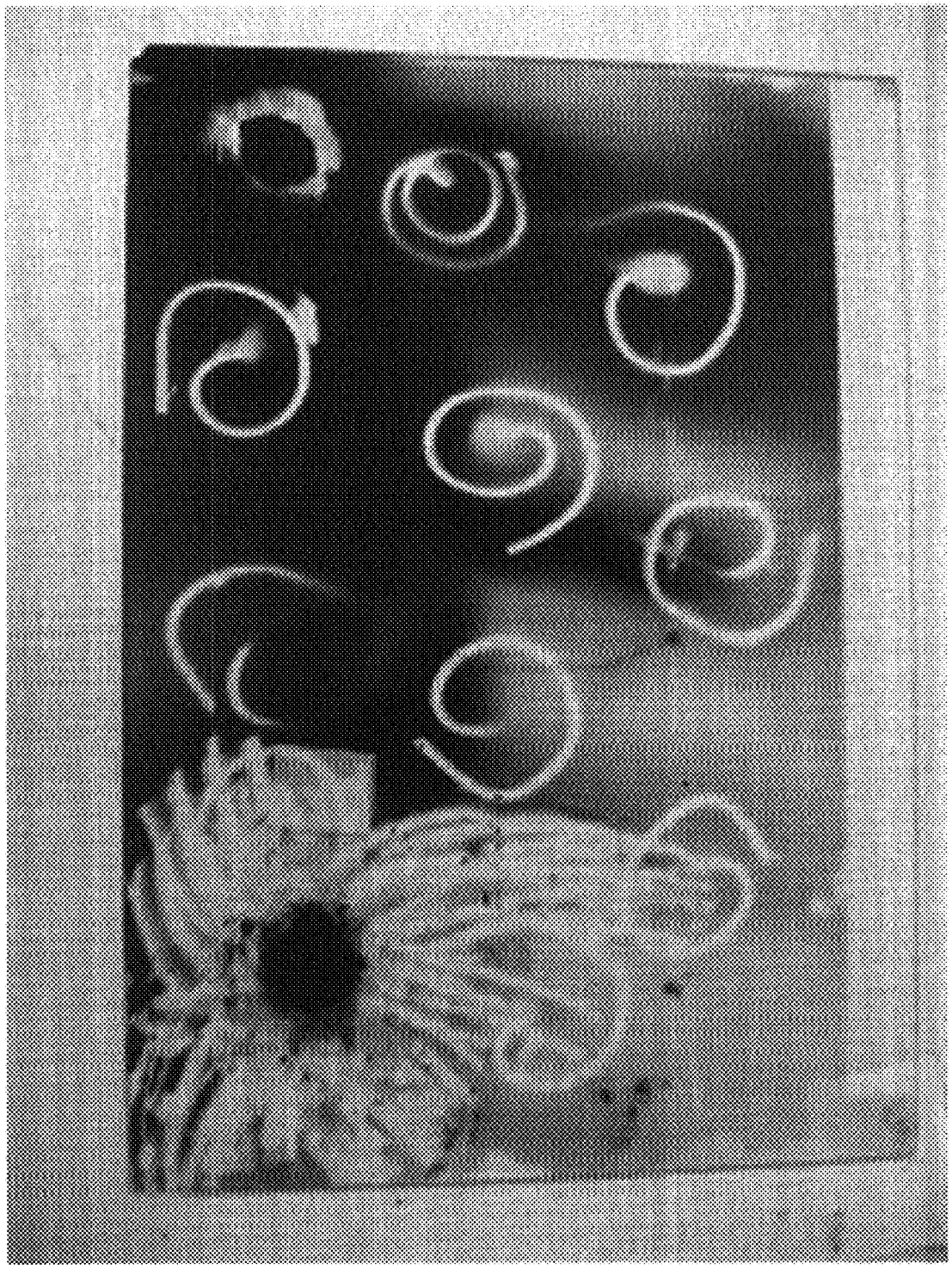
FIG. 7 illustrates the spores collected for color measurements.

Color of the spores is shown FIG. 6. Spores were collected from several mushrooms as scraped together for measurement of color (FIG. 7). The spores were covered with a glass plate to produce and even surface for color measurement using a Minolta chroma meter. The chroma meter was calibrated on an area without spores.

Discoloration of Flesh and Lamellae after Cutting the Mushrooms

Discoloration of flesh and lamallae is shown in FIG. 8. Cutting the mushrooms and leaving them for two hours at room temperature in a humid chamber resulted for all strains in discoloration of flesh and lamellae. Discoloration of lamellae was most pronounced for strain C9, producing yellow brownish lamellae. Lamellae of strains Broncoh and U1 remained reddish brown.

ADDITIONAL BOTANICAL DATA

Stipe/stem:

*Placement.*—The stipe is attached centrally to the cap.

*Shape.*—The stipe is cylindrical and slightly bulbous at the base.

*Size.*—The size of the stipe depends on the developmental stage at which it is harvested. When mushrooms are harvested at a young stage with a cap diameter of about 40 mm (cap not yet showing any signs of opening: i.e. harvested as commercial product), the height of the stipe varies between 13 and 24 mm (average: 17.7 mm, standard deviation 3.6 mm, n=20) the diameter of the stipe varies between 15 and 19 mm (average: 16.5 mm, standard deviation 1.0 mm, n=20).

*Color designation.*—The stipe is always white. Color of the stipe was measured using the (CIE) L*a*b system.

*Ring color designation.*—Cream white.

Gill:

*Characteristics.*—In mature mushrooms, the gills radiate from the site of attachment of the stipe outward to the margin of the cap. The basidia on the gills are predominantly bisporic.

*Color design.*—In young mushrooms where the veil is still intact, the gills are reddish brown (L=70.01, a=16.53 and b=13.50). As the mushroom matures the gills become darker brown, loosing the reddish teint.

Spore: Print: Strain 'Broncoh' produces chocolate brown spores.

*Color designation.*—Color of the spores is measured according to the L*a*b system, values being L=35.81, a=3.10 and b=5.75.

Veil:

*Form.*—The veils forms a ring around the stipe.

*Color designation.*—Cream white.

*Position.*—In young mushrooms a veil is present between the stipe and the margin of the cap, covering the gills. As the mushroom matures the veils stretches and breaks, remaining attached to the stipe.

Flesh color designation: The flesh of fresh cut mushrooms is measured according to the L*a*b system, values being L=89.99, a=2.00 and b=7.20 (white flesh).

Color designation of bruising/cutting: The tissue shows some discoloration upon injury. When color is allowed to develop over a period of 2 hours at room temperatuur in a humid chamber, color values according to the L*a*b system change slightly. L changes from 89.99 to 88.67, a changes from 2.00 to 3.08 and b changes from 7.20 to 6.73, resulting in a slightly reddish brown discoloration.

GROWTH CONDITIONS

The substrate compost consists of wheat straw, horse manure, gypsum and water and is fermented in tunnels in three phases. The substrate is inoculated with spawn. Spawn consists of grain (usually wheat) that is boiled in water, sterilized and inoculated with a pure culture of vegetative mycelium. After the grain is fully colonized, the spawn is stored at 4 to 8° C. in plastic bags of 15 kg before used to inoculate substrate. The spawn production is done in especially equipped plants on a large scale. Spawn is mixed with phase II compost and colonized in tunnels at 26° C. The full grown compost (spawn run compost) is transported to growing houses and filled in beds (usually two rows of shelves, 4 to 6 high, and 90 to 100 kg of compost/$m^2$). The growing houses are equipped with climate control systems. The fully colonized compost is covered with casing soil layer of approximately 5 cm thickness. The casing soil consists of peat and lime. After the colonization of the casing soil (10 days at 25° C., hardly no air movement) the climate in the growing house is changed to initiate fruiting body formation. The air temperature is decreased to 16–18° C. by venting the air (inlet of fresh air from outside the growing house). After 10 to 14 days, mushrooms are picked either by hand (for the fresh market) or cut and harvested mechanically (for canning). In the tests, all mushrooms were picked by hand.

BREEDING PROCESS HISTORY AND PROCEDURE

Three homokaryotic strains were used for breeding: two parental strains of the commercial white button mushroom, strain Horst U1 (homokaryon H39 and homokaryon H97); and a third homokaryon that was isolated from a wild brown strain. This homokaryon was isolated by protoplasting vegetative mycelium of the brown strain and recovering protoclones (colonies, each derived from a single regenerated protoplast). The used homokaryons are not derived from patented strains.

Both parental homokaryons of strain Horst U1 were crossed with the wild homokaryon. Fruit bodies were produced from each hybrid spores collected and single spore isolates (SSI's) obtained.

Using molecular markers, those SSI's were selected from the two parallel breeding lines that contained one nuclear type (homokaryon). From these SSI's, individuals were selected that had inherited the genetic markers linked to the cap color (brown variant) and the mating type (wild variant). From the latter selection, those SSI's were chosen that contained as much markers of the commercial homokaryons as possible. The homokaryons of both parallel breeding lines were crossed with the respective commercial homokaryon and the same marker assistant selection was carried out on the resulting SSI's, except that for the mating type marker the commercial variant was selected.

A selection of SSI's of one breeding line were crossed with a selection of the other breeding lines and the resulting hybrids were tested on 1.3 $m^2$ commercial compost in growing facilities in The Netherlands. Each hybrid was tested in 4 replicates. Yield, color, quality (shelf life), cultivation characteristics were, among other items, quantified.

The compost was produced in a tunnel of a compost producer and cultivation tests were done at three different mushroom farms under standard cultivation conditions (May, June 2003). Table 3 illustrates the yield of 'Broncoh' at three farms compared to a standard cultivation done in the same period in another growing house at the same location. Le Lion C9 was used as a commercial brown strain.

TABLE 3

| | Flush 1 | | Flush 2 | |
|---|---|---|---|---|
| | 'Broncoh' | Control | 'Broncoh' | Control |
| Grower 1 | 11.0 | 7.5 | 10.1 | 8.0 |
| Grower 2 | 13.5 | 9.2 | 7.9 | 7.8 |
| Grower 3 | 18.8 | 14.0 | 4.6 | 6.8 |

| | Flush 3 | | Total | | % |
|---|---|---|---|---|---|
| | 'Broncoh' | Control | 'Broncoh' | Control | increase |
| Grower 1 | 5.0 | 3.5 | 26.1 | 19.0 | 37.0% |
| Grower 2 | 2.7 | 2.8 | 24.1 | 19.8 | 21.7% |
| Grower 3 | 6.2 | 2.6 | 29.6 | 23.4 | 26.5% |

Yield in kg per square meters cultivation

MEDIA

The culture can be asexually reproduced on Malt extract medium (1% malt extract in 1% agar). This is done for the production of spawn. The culture is maintained in a collection as a mother culture on specially treated phase III compost. This is prepared from dried compost that is washed and sterilized before inoculation. The culture is stored at 2° C. on this medium and transferred once a year to fresh tubes. Alternatively, the culture is stored in liquid nitrogen.

I claim:

1. A new and distinct variety of *Agaricus bisporus Imbach*mushroom substantially as shown and described.

* * * * *

| | | Cap color | | | | | |
|---|---|---|---|---|---|---|---|
| | | Minimum | Maximum | Average | standard dev. | n | Color indication |
| Broncoh | L | 64.83 | 72.24 | 69.67 | 1.62 | 20 | |
| | a | 5.87 | 7.33 | 6.61 | 0.34 | 20 | |
| | b | 19.31 | 21.72 | 20.82 | 0.59 | 20 | |
| C9 | L | 59.46 | 66.20 | 63.41 | 2.11 | 20 | |
| | a | 7.60 | 9.27 | 8.55 | 0.40 | 20 | |
| | b | 17.80 | 20.94 | 19.55 | 0.83 | 20 | |
| U1 | L | 90.12 | 95.16 | 94.14 | 1.21 | 20 | |
| | a | 0.60 | 1.24 | 0.88 | 0.15 | 20 | |
| | b | 6.39 | 8.32 | 7.20 | 0.53 | 20 | |
| | | Stipe color | | | | | |
| | | Minimum | Maximum | Average | standard dev. | n | Color indication |
| Broncoh | L | 84.10 | 89.45 | 86.93 | 1.67 | 20 | |
| | a | 0.06 | 1.72 | 0.96 | 0.48 | 20 | |
| | b | 7.31 | 10.49 | 8.84 | 0.98 | 20 | |
| C9 | L | 82.87 | 90.56 | 87.58 | 1.73 | 20 | |
| | a | 0.09 | 1.83 | 0.57 | 0.54 | 20 | |
| | b | 7.74 | 15.78 | 9.37 | 1.78 | 20 | |
| U1 | L | 83.09 | 90.23 | 86.66 | 2.62 | 20 | |
| | a | 0.48 | 1.99 | 1.06 | 0.42 | 20 | |
| | b | 6.44 | 10.75 | 7.91 | 1.10 | 20 | |

Fig. 4

| Strain | L | a | b | Color indication |
|---|---|---|---|---|
| Broncoh | 35.81 | 3.10 | 5.75 | |
| C9 | 34.13 | 2.82 | 4.31 | |
| U1 | 36.96 | 3.25 | 6.66 | |

Fig. 6

| Strain | | Duration of storage (hrs) 0 | 2 | difference | Color indication 0 | 2 |
|---|---|---|---|---|---|---|
| | | | Discoloration of lamellae | | | |
| Bronc oh | L | 70.01 | 65.53 | 4.49 | | |
| | a | 16.53 | 16.99 | -0.46 | | |
| | b | 13.50 | 15.23 | -1.73 | | |
| C9 | L | 70.36 | 72.20 | -1.83 | | |
| | a | 17.01 | 3.99 | 13.02 | | |
| | b | 13.10 | 18.26 | -5.16 | | |
| U1 | L | 68.32 | 65.27 | 3.05 | | |
| | a | 19.57 | 18.82 | 0.75 | | |
| | b | 12.90 | 15.03 | -2.13 | | |
| | | | Discoloration of flesh | | | |
| Bronc oh | L | 89.99 | 88.67 | 1.32 | | |
| | a | 2.00 | 3.08 | -1.09 | | |
| | b | 7.20 | 6.73 | 0.48 | | |
| C9 | L | 89.91 | 89.97 | -0.06 | | |
| | a | 2.55 | 0.72 | 1.83 | | |
| | b | 7.13 | 7.22 | -0.09 | | |
| U1 | L | 89.93 | 89.03 | 0.89 | | |
| | a | 2.38 | 3.29 | -0.92 | | |
| | b | 7.20 | 6.70 | 0.50 | | |

Fig. 8